United States Patent [19]

Bundy

[11] 4,145,561

[45] Mar. 20, 1979

[54] 2-DECARBOXY-2-HYDROXYMETHYL-9-DEOXY-9-METHYLENE-16-PHENYL-PGF COMPOUNDS

[75] Inventor: Gordon L. Bundy, Portage, Mich.

[73] Assignee: The Upjohn Company, Kalamazoo, Mich.

[21] Appl. No.: 924,036

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ .................................... C07C 177/00
[52] U.S. Cl. ............................. 568/807; 568/644; 568/645; 568/646; 568/660
[58] Field of Search .................................... 568/807

[56] References Cited

U.S. PATENT DOCUMENTS

| | | | |
|---|---|---|---|
| 3,931,299 | 1/1976 | Strike | 260/514 D |
| 3,950,363 | 4/1976 | Bundy | 260/347.3 |
| 4,060,534 | 11/1977 | Bundy | 260/408 |

Primary Examiner—Gerald A. Schwartz
Attorney, Agent, or Firm—Robert A. Armitage

[57] ABSTRACT

The present invention relates to novel 2-decarboxy-2-hydroxymethyl-9-deoxy-9-methylene-16-phenyl-PGF compounds. These compounds are useful pharmacological agents, and are useful for the same purposes as the corresponding PGE-type compounds.

121 Claims, No Drawings

2-DECARBOXY-2-HYDROXYMETHYL-9-DEOXY-9-METHYLENE-16-PHENYL-PGF COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to novel 2-decarboxy-2-hydroxymethyl-9-deoxy-9-methylene-16-phenyl-PGF compounds, the essential material constituting a disclosure of which is incorporated here by reference from U.S. Pat. 4,118,584.

I claim:

1. A prostaglandin analog of the formula

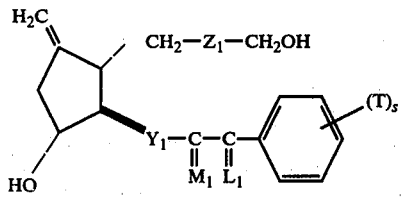

wherein
$Y_1$ is trans-CH=CH— or —CH$_2$CH$_2$—;
wherein
$M_1$ is

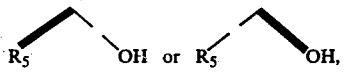

wherein
$R_5$ is hydrogen or methyl;
wherein
$L_1$ is

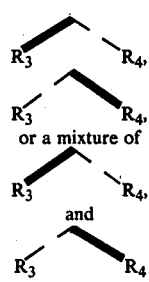

wherein $R_3$ and $R_4$ are hydrogen, methyl, or fluoro, being the same or different, with the provisio that one of $R_3$ and $R_4$ is fluoro only when the other is hydrogen or fluoro; wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$— or
(5) —(CH$_2$)$_3$—(CH$_2$)$_g$—CF$_2$—
wherein g is one, 2, or 3; and
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl.

2. A prostaglandin analog according to claim 1, wherein $Y_1$ is —CH$_2$CH$_2$—.

3. A prostaglandin analog according to claim 2, wherein $Z_1$ is cis—CH$_2$—CH=CH—(CH$_2$)$_g$—CH$_2$—.

4. 2-Decarboxy-2-hydroxymethyl-9-deoxy-9-methylene-cis-4,5-didehydro-16-phenyl-17,18,19,20-tetranor-13,14-dihydro-PGF$_1$, a prostaglandin analog according to claim 3.

5. A prostaglandin analog according to claim 2, wherein $Z_1$ is —(CH$_2$)$_3$—(CH$_2$)$_g$—CH$_2$—.

6. A prostaglandin analog according to claim 5, wherein $M_1$ is

7. 2-Decarboxy-2-hydroxymethyl-9-deoxy-9-methylene-15-epi-16-phenyl-17,18,19,20-tetranor-13,14-dihydro-PGF$_1$, a prostaglandin analog according to claim 6.

8. A prostaglandin analog according to claim 5, wherein $M_1$ is

9. A prostaglandin analog according to claim 8, wherein s is zero or one and T is chloro, fluoro, or trifluoromethyl.

10. A prostaglandin analog according to claim 9, wherein g is 3.

11. 2-Decarboxy-2-hydroxymethyl-9-deoxy-9-methylene-2a,2b-dihomo-15-methyl-16-phenyl-17,18,19,20-tetranor-13,14-dihydro-PGF$_1$, a prostaglandin analog according to claim 10.

12. 2-Decarboxy-2-hydroxymethyl-9-deoxy-9-methylene-2a,2b-dihomo-16-phenyl-17,18,19,20-tetranor-13,14-dihydro-PGF$_1$, a prostaglandin analog according to claim 10.

13. A prostaglandin analog according to claim 9, wherein g is one.

14. A prostaglandin analog according to claim 13, wherein at least one of $R_3$ and $R_4$ is methyl.

15. A prostaglandin analog according to claim 14, wherein $R_3$ and $R_4$ are both methyl.

16. 2-Decarboxy-2-hyroxymethyl-9-deoxy-9-methylene-16-methyl-16-phenyl-18,19,20-trinor-13,14-dihydro-PGF$_1$, a prostaglandin analog according to claim 15.

17. A prostaglandin analog according to claim 13, wherein at least one of $R_3$ and $R_4$ is fluoro.

18. A prostaglandin analog according to claim 17, wherein $R_3$ and $R_4$ are both fluoro.

19. 2-Decarboxy-2-hydroxymethyl-9-deoxy-9-methylene-16,16-difluoro-16-phenyl-17,18,19,20-tetranor-13,14-dihydro-PGF$_1$, a prostaglandin analog according to claim 18.

20. A prostaglandin analog according to claim 13, wherein $R_3$ and $R_4$ are both hydrogen.

21. A prostaglandin analog according to claim 20, wherein $R_5$ is methyl.

22. 2-Decarboxy-2-hydroxymethyl-9-deoxy-9-methylene-15-methyl-16-phenyl-17,18,19,20-tetranor-13,14-dihydro-PGF$_1$, a prostaglandin analog according to claim 21.

23. A prostaglandin analog according to claim 20, wherein $R_5$ is hydrogen.

24. 2-Decarboxy-2-hydroxymethyl-9-deoxy-9-methylene-16-phenyl-17,18,19,20-tetranor-13,14-dihydro-PGF$_1$, a prostaglandin analog according to claim 23.

25. A prostaglandin analog according to claim 2, wherein Z$_1$ is cis—CH=CH—CH$_2$—(CH$_2$)$_g$—CH$_2$—.

26. A prostaglandin analog according to claim 25, wherein M$_1$ is

27. A prostaglandin analog according to claim 26, wherein s is zero or one and T is chloro, fluoro, or trifluoromethyl.

28. A prostaglandin analog according to claim 27, wherein g is 3.

29. 2-Decarboxy-2-hydroxymethyl-9-deoxy-9-methylene-2a,2b-dihomo-15-epi-15-methyl-16-phenyl-17,18,19,20-tetranor-13,14-dihydro-PGF$_2$, a prostaglandin analog according to claim 28.

30. 2-Decarboxy-2-hydroxymethyl-9-methylene-2—a,2b-dihomo-15-epi-16-phenyl-17,18,19,20-tetranor-13,14-dihydro-PGF$_2$, a prostaglandin analog according to claim 28.

31. A prostaglandin analog according to claim 27, wherein g is one.

32. A prostaglandin analog according to claim 31, wherein at least one of R$_3$ and R$_4$ is methyl.

33. 2-Decarboxy-2-hydroxymethyl-9-deoxy-9-methylene-15-epi-16-methyl-16-phenyl-18,19,20-trinor-13,14-dihydro-PGF$_2$, a prostaglandin analog according to claim 32.

34. A prostaglandin analog according to claim 31, wherein at least one of R$_3$ and R$_4$ is fluoro.

35. 2-Decarboxy-2-hydroxymethyl-9-deoxy-9-methylene-15-epi-16,16-difluoro-16-phenyl-17,18,19,20-tetranor-13,14-dihydro-PGF$_2$, a prostaglandin analog according to claim 34.

36. A prostaglandin analog according to claim 31, wherein R$_3$ and R$_4$ are both hydrogen.

37. 2-Decarboxy-2-hyroxymethyl-9-deoxy-9-methylene-15-epi-16-phenyl-17,18,19,20-tetranor-13,14-dihydro-PGF$_2$, a prostaglandin analog according to claim 36.

38. A prostaglandin analog according to claim 25, wherein M$_1$ is

39. A prostaglandin analog according to claim 38, wherein s is zero and T is chloro, fluoro, or trifluoromethyl.

40. A prostaglandin analog according to claim 39, wherein g is 3.

41. A prostaglandin analog according to claim 40, wherein at least one of R$_3$ and R$_4$ is methyl.

42. 2-Decarboxy-2-hyroxymethyl-9-deoxy-9-methylene-2a,2b-dihomo-16-methyl-16-phenyl-18,19,20-trinor-13,14-dihydro-PGF$_2$, a prostaglandin analog according to claim 41.

43. A prostaglandin analog according to claim 40, wherein at least one of R$_3$ and R$_4$ is fluoro.

44. 2-Decarboxy-2-hydroxymethyl-9-deoxy-9-methylene-2a,2b-dihomo-16,16-difluoro-16-phenyl-17,18,19,20-tetranor-13,14-dihydro-PGF$_2$, a prostaglandin analog according to claim 43.

45. A prostaglandin analog according to claim 40, wherein R$_3$ and R$_4$ ae both hydrogen.

46. 2-Decarboxy-2-hydroxymethyl-9-deoxy-9-methylene-2a,2b-dihomo-16-phenyl-17,18,19,20-tetranor-13,14-dihydro-PGF$_2$, a prostaglandin analog according to claim 45.

47. A prostaglandin analog according to claim 29, wherein g is one.

48. A prostaglandin analog according to claim 47, wherein at least one of R$_3$ and R$_4$ is methyl.

49. A prostaglandin analog according to claim 48, wherein R$_3$ and R$_4$ are both methyl.

50. 2-Decarboxy-2-hyroxymethyl-9-deoxy-9-methylene-16-methyl-16-phenyl-18,19,20-trinor-13,14-dihydro-PGF$_2$, a prostaglandin analog according to claim 49.

51. A prostaglandin analog according to claim according to claim 47, wherein at least one of R$_3$ and R$_4$ is fluoro.

52. A prostaglandin analog according to claim 51, wherein R$_3$ and R$_4$ are both fluoro.

53. A prostaglandin analog according to claim 52, wherein R$_5$ is methyl.

54. 2-Decarboxy-2-hydroxymethyl-9-deoxy-9-methylene-15-methyl-16,16-difluoro-16-phenyl-17,18,19,20-tetranor-13,14-dihydro-PGF$_2$, a prostaglandin analog according to claim 53.

55. A prostaglandin analog according to claim 52, wherein R$_5$ is hydrogen.

56. 2-Decarboxy-2-hydroxymethyl-9-deoxy-9-methylene-16,16-difluoro-16-phenyl-17,18,19,20-tetranor-13,14-dihydro-PGF$_2$, a prostaglandin analog according to claim 55.

57. A prostaglandin analog according to claim 47, wherein R$_3$ and R$_4$ are both hydrogen.

58. A prostaglandin analog according to claim 57, wherein R$_5$ is methyl.

59. 2-Decarboxy-2-hydroxymethyl-9-deoxy-9-methylene-15-methyl-16-phenyl-17,18,19,20-tetranor-13,14-dihydro-PGF$_2$, a prostaglandin analog according to claim 58.

60. A prostaglandin analog according to claim 57, wherein R$_5$ is hydrogen.

61. 2-Decarboxy-2-hydroxymethyl-9-deoxy-9-methylene-16-phenyl-17,18,19,20-tetranor-13,14-dihydro-PGF$_2$, a prostaglandin analog according to claim 60.

62. A prostaglandin analog according to claim 1, wherein Y$_1$ is trans—CH=CH—.

63. A prostaglandin analog according to claim 62, wherein Z$_1$ is cis—CH$_2$—CH=CH—(CH$_2$)$_g$—CH$_2$—.

64. 2-Decarboxy-2-hyroxymethyl-9-deoxy-9-methylene-cis-4,5-didehydro-16-phenyl-17,18,19,20-tetranor-PGF$_1$, a prostaglandin analog according to claim 63.

65. A prostaglandin analog according to claim 62, wherein Z$_1$ is —(CH$_2$)$_3$—(CH$_2$)$_g$—CH$_2$—.

66. A prostaglandin analog according to claim 65, wherein M$_1$ is

67. 2-Decarboxy-2-hydroxymethyl-9-deoxy-9-methylene-15-epi-16-phenyl-17,18,19,20-tetranor-PGF$_1$, a prostaglandin analog according to claim 66.

68. A prostaglandin analog according to claim 65, wherein $M_1$ is

69. A prostaglandin analog according to claim 68, wherein s is zero or one and T is chloro, fluoro, or trifluoromethyl.

70. A prostaglandin analog according to claim 69, wherein g is 3.

71. 2-Decarboxy-2-hydroxymethyl-9-deoxy-9-methylene-2a,2b-dihomo-15-methyl-16-phenyl-17,18,19,20-tetranor-PGF$_1$, a prostaglandin analog according to claim 70.

72. 2-Decarboxy-2-hydroxymethyl-9-deoxy-9-methylene-2a,2b-dihomo-16-phenyl-17,18,19,20-tetranor-PGF$_1$, a prostaglandin analog according to claim 70.

73. A prostaglandin analog according to claim 69, wherein g is one.

74. A prostaglandin analog according to claim 73, wherein at least one of $R_3$ and $R_4$ is methyl.

75. A prostaglandin analog according to claim 74, wherein $R_3$ and $R_4$ are both methyl.

76. 2-Decarboxy-2-hyroxymethyl-9-deoxy-9-methylene-16-methyl-16-phenyl-18,19,20-trinor-PGF$_1$, a prostaglandin analog according to claim 75.

77. A prostaglandin analog according to claim 73, wherein at least one of $R_3$ and $R_4$ is fluoro.

78. A prostaglandin analog according to claim 77, wherein $R_3$ and $R_4$ are both fluoro.

79. 2-Decarboxy-2-hydroxymethyl-9-deoxy-9-methylene-16,16-difluoro-16-phenyl-17,18,19,20-tetranor-PGF$_1$, a prostaglandin analog according to claim 78.

80. A prostaglandin analog according to claim 73, wherein $R_3$ and $R_4$ are both hydrogen.

81. A prostaglandin analog according to claim 80, wherein $R_5$ is methyl.

82. 2-Decarboxy-2-hydroxymethyl-9-deoxy-9-methylene-15-methyl-16-phenyl-17,18,19,20-tetranor-PGF$_1$, a prostaglandin analog according to claim 81.

83. A prostaglandin analog according to claim 80, wherein $R_5$ is hydrogen.

84. 2-Decarboxy-2-hydroxymethyl-9-deoxy-9-methylene-16-phenyl-17,18,19,20-tetranor-PGF$_1$, a prostaglandin analog according to claim 83.

85. A prostaglandin analog according to claim 62, wherein $Z_1$ is cis—CH═CH—CH$_2$—(CH$_2$)$_g$—CH$_2$—.

86. A prostaglandin analog according to claim 85, wherein $M_1$ is

87. A prostaglandin analog according to claim 86, wherein s is zero or one and T is chloro, fluoro, or trifluoromethyl.

88. A prostaglandin analog according to claim 87, wherein g is 3.

89. 2-Decarboxy-2-hydroxymethyl-9-deoxy-9-methylene-2a,2b-dihomo-15-epi-15-methyl-16-phenyl-17,18,19,20-tetranor-PGF$_2$, a prostaglandin analog according to claim 88.

90. 2-Decarboxy-2-hydroxymethyl-9-deoxy-9-methylene-2a,2b-dihomo-15-epi-16-phenyl-17,18,19,20-tetranor-PGF$_2$, a prostaglandin analog according to claim 88.

91. A prostaglandin analog according to claim 87, wherein g is one.

92. A prostaglandin analog according to claim 91, wherein at least one of $R_3$ and $R_4$ is methyl.

93. 2-Decarboxy-2-hydroxymethyl-9-deoxy-9-methylene-15-epi-16-methyl-16-phenyl-18,19,20-trinor-PGF$_2$, a prostaglandin analog according to claim 92.

94. A prostaglandin analog according to claim 91, wherein at least one of $R_3$ and $R_4$ is fluoro.

95. 2-Decarboxy-2-hydroxymethyl-9-deoxy-9-methylene-15-epi-16,16-difluoro-16-phenyl-17,18,19,20-tetranor-PGF$_2$, a prostaglandin analog according to claim 94.

96. A prostaglandin analog according to claim 91, wherein $R_3$ and $R_4$ are both hydrogen.

97. 2-Decarboxy-2-hydroxymethyl-9-deoxy-9-methylene-15-epi-15-methyl-16-phenyl-17,18,19,20-tetranor-PGF$_2$, a prostaglandin analog according to claim 96.

98. A prostaglandin analog according to claim 85, wherein $M_1$ is

99. A prostaglandin analog according to claim 98, wherein s is zero or one and T is chloro, fluoro, or trifluoromethyl.

100. A prostaglandin analog according to claim 99, wherein g is 3.

101. A prostaglandin analog according to claim 100, wherein at least one of $R_3$ and $R_4$ is methyl.

102. 2-Decarboxy-2-hydroxymethyl-9-deoxy-9-methylene-2a,2b-dihomo-16-methyl-16-phenyl-18,19,20-trinor-PGF$_2$, a prostaglandin analog according to claim 101.

103. A prostaglandin analog according to claim 100, wherein at least one of $R_3$ and $R_4$ is fluoro.

104. 2-Decarboxy-2-hydroxymethyl-9-deoxy-9-methylene-2a,2b-dihomo-16,16-difluoro-16-phenyl-17,18,19,20-tetranor-PGF$_2$, a prostaglandin analog according to claim 101.

105. A prostaglandin analog according to claim 100, wherein $R_3$ and $R_4$ are both hydrogen.

106. 2-Decarboxy-2-hydroxymethyl-9-deoxy-9-methylene-2a,2b-dihomo-15-methyl-16-phenyl-17,18,19,20-tetranor-PGF$_2$, a prostaglandin analog according to claim 105.

107. A prostaglandin analog according to claim 99, wherein g is one.

108. A prostaglandin analog according to claim 107, wherein at least one of $R_3$ and $R_4$ is methyl.

109. A prostaglandin analog according to claim 108, wherein $R_3$ and $R_4$ are both methyl.

110. 2-Decarboxy-2-hydroxymethyl-9-deoxy-9-methylene-16-methyl-16-phenyl-18,19,20-trinor-PGF$_2$, a prostaglandin analog according to claim 109.

111. A prostaglandin analog according to claim 107, wherein at least one of $R_3$ and $R_4$ is fluoro.

112. A prostaglandin analog according to claim 111, wherein $R_3$ and $R_4$ are both fluoro.

113. A prostaglandin analog according to claim 112, wherein $R_5$ is methyl.

114. 2-Decarboxy-2-hydroxymethyl-9-deoxy-9-methylene-15-methyl-16,16-difluoro-16-phenyl-17,18,19,20-tetranor-PGF$_2$, a prostaglandin analog according to claim 113.

115. A prostaglandin analog according to claim 112, wherein $R_5$ is hydrogen.

116. 2-Decarboxyl-2-hydroxymethyl-9-deoxy-9-methylene-16,16-difluoro-16-phenyl-17,18,19,20-tetranor-PGF$_2$, a prostaglandin analog according to claim 115.

117. A prostaglandin analog according to claim 115, wherein R$_3$ and R$_4$ are both hydrogen.

118. A prostaglandin analog according to claim 117, wherein R$_5$ is methyl.

119. 2-Decarboxy-2-hydroxymethyl-9-deoxy-9-methylene-15-methyl-16-phenyl-17,18,19,20-tetranor-PGF$_2$, a prostaglandin analog according to claim 118.

120. A prostaglandin analog according to claim 117, wherein R$_5$ is hydrogen.

121. 2-Decarboxy-2-hydroxymethyl-9-deoxy-9-methylene-16-phenyl-17,18,19,20-tetranor-PGF$_2$, a prostaglandin analog according to claim 120.

* * * * *

UNITED STATES PATENT AND TRADEMARK OFFICE
CERTIFICATE OF CORRECTION

PATENT NO. : 4,145,561
DATED : March 20, 1979
INVENTOR(S) : Gordon L. Bundy

It is certified that error appears in the above-identified patent and that said Letters Patent are hereby corrected as shown below:

Column 3, lines 22-23, "9-methylene-2—a,2b-dihomo" should read -- 9-deoxy-9-methylene-2a,2b-dihomo --.

Signed and Sealed this

Thirty-first Day of July 1979

[SEAL]

Attest:

Attesting Officer

LUTRELLE F. PARKER
Acting Commissioner of Patents and Trademarks